(12) United States Patent
Waterbury et al.

(10) Patent No.: US 6,197,826 B1
(45) Date of Patent: Mar. 6, 2001

(54) α-(2-HYDROXYPHENYL) NITRONE COMPOUNDS, PHARMACEUTICAL COMPOSITIONS CONTAINING THE SAME AND METHODS FOR TREATING INFLAMMATION

(75) Inventors: L. David Waterbury, San Carlos; John M. Carney, Saratoga; Allan L. Wilcox, Mountain View, all of CA (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/354,577

(22) Filed: Jul. 16, 1999

Related U.S. Application Data

(60) Provisional application No. 60/093,237, filed on Jul. 17, 1998.

(51) Int. Cl.[7] .......................... A01N 33/24; C07C 249/00
(52) U.S. Cl. .......................... 514/640; 514/645; 564/265; 564/300
(58) Field of Search .................... 514/640, 645; 564/265, 300

(56) References Cited

U.S. PATENT DOCUMENTS

| | | |
|---|---|---|
| 3,917,700 | 11/1975 | Auerbach . |
| 4,128,664 | 12/1978 | Moore . |
| 4,153,722 | 5/1979 | Campbell et al. . |
| 5,288,896 | 2/1994 | Capiris et al. . |
| 5,397,789 | 3/1995 | Carr et al. . |
| 5,455,272 | 10/1995 | Janzen et al. . |
| 5,527,828 | 6/1996 | Janzen et al. . |
| 5,532,277 | 7/1996 | Janze et al. . |
| 5,942,507 | 8/1999 | Kelleher et al. . |
| 5,972,977 | 10/1999 | Narducy et al. . |
| 5,994,396 | 11/1999 | Kelleher et al. . |
| 5,998,469 | 12/1999 | Kelleher et al. . |
| 6,015,831 | 1/2000 | Kelleher et al. . |

FOREIGN PATENT DOCUMENTS

| | | |
|---|---|---|
| 2137619 | 10/1984 | (GB) . |
| WO 91/05552 | 5/1991 | (WO) . |
| WO 92/22290 | 12/1992 | (WO) . |
| WO 95/11227 | 4/1995 | (WO) . |
| WO 97/39751 | 10/1997 | (WO) . |
| WO 99/20601 | 4/1999 | (WO) . |

OTHER PUBLICATIONS

Fevig, T.L. et al. "Design, Synthesis and in vitro Evaluation of Cyclic Nitrones as Free Radical Traps for the Treatment of Stock." *J. Med. Chem.* 1996, 39, 4988–4996.

*Primary Examiner*—Paul J. Killos
(74) *Attorney, Agent, or Firm*—Burns, Doane, Swecker & Mathis, LLP

(57) ABSTRACT

Disclosed are novel α-(2-hydroxyphenyl) nitrone compounds and pharmaceutical compositions containing such compounds. The disclosed compositions are useful as therapeutics for inflammation-related conditions in mammals, such as arthritis, and as analytical reagents for detecting free radicals.

40 Claims, No Drawings

α-(2-HYDROXYPHENYL) NITRONE COMPOUNDS, PHARMACEUTICAL COMPOSITIONS CONTAINING THE SAME AND METHODS FOR TREATING INFLAMMATION

CROSS-REFERENCE TO RELATED APPLICATIONS

This application claims the benefit of U.S. Ser. No. 60/093,237, filed Jul. 17, 1998, the disclosure of which is incorporated herein by reference in its entirety.

BACKGROUND OF THE INVENTION

1. Field of the Invention

This invention relates to novel α-(2-hydroxyphenyl) nitrone compounds and their use as therapeutic agents for the treatment of inflammation-related conditions in mammals, such as arthritis, and as analytical reagents for detecting free radicals.

2. State of the Art

Arthritis and related inflammatory disease conditions occur in more than 100 different forms, including rheumatoid arthritis (RA), osteoarthritis (OA), ankylosing spondylitis and systemic lupus erythematosus (SLE). Most forms of arthritis are characterized by some type of chronic inflammation. For example, RA typically involves chronic inflammation of the lining of the joints and/or the internal organs. Such chronic inflammation generally causes pain and swelling in the joints of those afflicted and may result in damage to cartilage, bone, tendons, ligaments and the like, ultimately leading to deformity and disability.

Prostaglandins have long been known to be involved in the inflammation process. Accordingly, a number of inhibitors of prostaglandin synthesis have been developed for the treatment of arthritis and related inflammatory disease conditions. Such non-steroidal antiinflammatory drugs (NSAIDS) typically prevent the production of prostaglandins by inhibiting enzymes in the human arachidonic acid/prostaglandin pathway, including the enzyme cycloxygenase (COX). The enzyme COX is known to exist in two forms. COX-1 is a constitutive form of the enzyme found in most tissues and organs. Among other properties, COX-1 produces relatively small amounts of prostoglandins necessary for maintaining the integrity of the gastrointestinal tract. COX-2, on the other hand, is an inducible form of the enzyme associated with the increased production of prostoglandins during inflammatory conditions. Since many NSAIDS inhibit both forms of COX, they interfere with prostaglandin-regulated processes not associated with the inflammation process. As a result, many NSAIDS cause severe side effects, such as stomach ulcers and renal damage, which limit their effectiveness as therapeutics.

Accordingly, a need exists for novel classes of therapeutic compounds which effectively treat arthritis and other inflammation-related conditions without producing undesired side effects.

SUMMARY OF THE INVENTION

This invention provides novel α-(2-hydroxyphenyl) nitrone compounds which are useful as therapeutics for reducing inflammation in mammals. In particular, the compounds of this invention are useful for treating arthritis and other inflammation-related conditions.

Accordingly, in one of its composition aspects, this invention is directed to compounds of formula I:

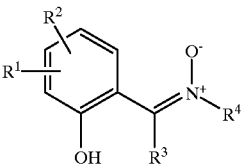

wherein $R^1$ is selected from the group consisting of alkyl, alkenyl, alkoxy, acylamino, amino, substituted amino, aryl, cycloalkyl, halogen, nitro and —C=N(O)—$R^5$, wherein $R^5$ is alkyl, substituted alkyl or cycloalkyl;

$R^2$ is selected from the group consisting of hydrogen, alkyl, alkenyl, alkoxy, acylamino, amino, substituted amino, aryl, cycloalkyl, halogen and nitro; or $R^1$ and $R^2$ can be joined together to form an alkylenedioxy group;

$R^3$ is selected from the group consisting of hydrogen, alkyl and aryl; and $R^4$ is selected from the group consisting of alkyl, substituted alkyl and cycloalkyl; and pharmaceutically acceptable salts thereof.

Preferably, $R^1$ is selected from the group consisting of alkoxy, alkyl, halogen, nitro and —CH=N(O)—$R^5$, wherein $R^5$ is alkyl, substituted alkyl or cycloalkyl. More preferably, $R^1$ is alkyl. Examples of preferred $R^1$ groups include, but are not limited to, tert-butyl, bromo, fluoro, chloro, methyl, methoxy, nitro and [(tert-butyl)oxidoimino]methyl. A particularly preferred $R^1$ group is tert-butyl.

$R^2$ is preferably selected from the group consisting of alkoxy, alkyl and halogen. More preferably, $R^2$ is alkyl. Examples of preferred $R^2$ groups include, but are not limited to, hydrogen, tert-butyl, bromo, chloro, methoxy and methyl. A particularly preferred $R^2$ group is tert-butyl.

When $R^1$ and $R^2$ are attached to adjacent carbon atoms, $R^1$ and $R^2$ are also preferably joined together to form an alkylenedioxy group having 1 to about 6 carbon atoms, more preferably 1 or 2 carbon atoms. Particularly preferred alkylenedioxy groups include methylenedioxy and ethylenedioxy.

$R^3$ is preferably hydrogen or lower alkyl. More preferably, $R^3$ is hydrogen or alkyl having 1 to 4 carbon atoms, more preferably 1 or 2 carbon atoms. Still more preferably, $R^3$ is hydrogen.

$R^4$ is preferably selected from the group consisting of alkyl having 3 to about 8 carbon atoms and cycloalkyl having 3 to about 8 carbon atoms. More preferably, $R^4$ is alkyl having 3 to 6 carbon atoms or cycloalkyl having 5 to 6 carbon atoms. Particularly preferred $R^4$ groups include n-propyl, isopropyl, n-butyl, tert-butyl and cyclohexyl.

$R^5$ is preferably selected from the group consisting of alkyl having 3 to about 8 carbon atoms and cycloalkyl having 3 to about 8 carbon atoms. More preferably, $R^5$ is alkyl having 3 to 6 carbon atoms or cycloalkyl having 5 to 6 carbon atoms. Particularly preferred $R^5$ groups include n-propyl, isopropyl, n-butyl, tert-butyl and cyclohexyl.

In a preferred embodiment, this invention is directed to a compound of formula II:

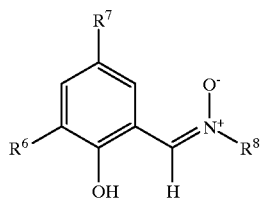

II wherein

R⁶ is selected from the group consisting of alkyl and cycloalkyl;

R⁷ is selected from the group consisting of alkyl and cycloalkyl; and

R⁸ is selected from the group consisting of alkyl, substituted alkyl and cycloalkyl; and pharmaceutically acceptable salts thereof.

Preferably, $R^6$ and $R^7$ are the same or different and each is independently selected from an alkyl group having from 1 to about 6 carbon atoms. More preferably, $R^6$ and $R^7$ are independently selected from the group consisting of methyl, ethyl, n-propyl, isopropyl, n-butyl, isobutyl, sec-butyl and tert-butyl. Still more preferably, $R^6$ and $R^7$ are both tert-butyl.

$R^8$ is preferably selected from the group consisting of alkyl having 3 to about 8 carbon atoms and cycloalkyl having 3 to about 8 carbon atoms. More preferably, $R^8$ is alkyl having 3 to 6 carbon atoms or cycloalkyl having 5 to 6 carbon atoms. Particularly preferred $R^8$ groups include n-propyl, isopropyl, n-butyl, tert-butyl and cyclohexyl.

Particularly preferred α-(2-hydroxyphenyl) nitrone compounds include those having the formula shown in Table I.

Accordingly, in another of its composition aspects, this invention is directed to each of the individual compounds:

α-(5-chloro-2-hydroxyphenyl)-N-tert-butylnitrone
α-(3,5-di-tert-butyl-2-hydroxyphenyl)-N-tert-butylnitrone
α-(3,5-dibromo-2-hydroxyphenyl)-N-tert-butylnitrone
α-(3-fluoro-2-hydroxyphenyl)-N-tert--butylnitrone
α-{3-[(tert-butyl)oxidoimino]methyl-2-hydroxy-5-methylphenyl)}-N-tert-butylnitrone
α-(2-hydroxy-3-methylphenyl)-N-tert-butylnitrone
α-{3-[(tert-butyl)oxidoimino]methyl-5-chloro-2-hydroxyphenyl)}-N-tert-butylnitrone
α-(2-hydroxy-5-methoxyphenyl)-N-tert-butylnitrone
α-(2-hydroxy-5-nitrophenyl)-N-tert-butylnitrone
α-(3-ethoxy-2-hydroxyphenyl)-N-tert-butylnitrone
α-(2-hydroxy-4-methoxyphenyl)-N-tert-butylnitrone
α-(4-N,N-diethylamino-2-hydroxyphenyl)-N-tert-butylnitrone
α-(3,5-dichloro-2-hydroxyphenyl)-N-tert-butylnitrone
α-(4,6-dimethoxy-2-hydroxyphenyl)-N-tert-butylnitrone
α-(2-hydroxy-5-trifluoromethoxyphenyl)-N-tert-butylnitrone
α-(3,5-diiodo-2-hydroxyphenyl)-N-tert-butylnitrone
α-(3,5-dinitro-2-hydroxyphenyl)-N-tert-butylnitrone and pharmaceutically acceptable salts thereof.

In another of its composition aspects, this invention is directed to pharmaceutical compositions comprising a pharmaceutically acceptable carrier and a pharmaceutically effective amount of a compound of formula I:

TABLE I

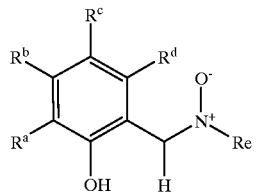

| No. | Rᵃ | Rᵇ | Rᶜ | Rᵈ | Rᵉ |
|---|---|---|---|---|---|
| 1 | —H | —H | —Cl | —H | —C(CH₃)₃ |
| 2 | —C(CH₃)₃ | —H | —C(CH₃)₃ | —H | —C(CH₃)₃ |
| 3 | —Br | —H | —Br | —H | —C(CH₃)₃ |
| 4 | —F | —H | —H | —H | —C(CH₃)₃ |
| 5 | —CH═N(O)—C(CH₃)₃ | —H | —CH₃ | —H | —C(CH₃)₃ |
| 6 | —CH₃ | —H | —H | —H | —C(CH₃)₃ |
| 7 | —CH═N(O)—C(CH₃)₃ | —H | —Cl | —H | —C(CH₃)₃ |
| 8 | —H | —H | —OCH₃ | —H | —C(CH₃)₃ |
| 9 | —H | —H | —NO₂ | —H | —C(CH₃)₃ |
| 10 | —OCH₂CH₃ | —H | —H | —H | —C(CH₃)₃ |
| 11 | —H | —OCH₃ | —H | —H | —C(CH₃)₃ |
| 12 | —H | —N(CH₂CH₃)₂ | —H | —H | —C(CH₃)₃ |
| 13 | —Cl | —H | —Cl | —H | —C(CH₃)₃ |
| 14 | —H | —H | —Br | —H | —C(CH₃)₃ |
| 15 | —H | —OCH₃ | —H | —OCH₃ | —C(CH₃)₃ |
| 16 | —H | —H | —OCF₃ | —H | —C(CH₃)₃ |
| 17 | —I | —H | —I | —H | —C(CH₃)₃ |
| 18 | —H | —OCH₃ | —H | —H | —C(CH₃)₃ |

I wherein R¹–R⁴ are as defined above.

In additional composition aspects, this invention is directed to pharmaceutical compositions comprising a pharmaceutically acceptable carrier and a pharmaceutically effective amount of a compound of formula II above.

Among other properties, the α-(2-hydroxyphenyl) nitrone compounds of this invention have been discovered to inhibit the induction of cyclooxygenase associated with prostagladin $E_2$ ($PGE_2$) synthesis and inflammation. Compounds having such properties are useful for reducing inflammation, including inflammation resulting from arthritis and related inflammatory conditions.

Accordingly, in one of its method aspects, this invention is directed to a method for treating a mammal with an inflammation-related condition which method comprises administering to said patient a pharmaceutical composition comprising a pharmaceutically acceptable carrier and an effective inflammation-reducing amount of a compound of formula I or II above.

In preferred embodiments of this invention, the inflammation-related condition treated in the above methods is rheumatoid arthritis, osteoarthritis, ankylosing spondylitis, systemic lupus erythematosus, psoriatic arthritis, and the like.

DETAILED DESCRIPTION OF THE INVENTION

For the purposes of this invention, the α-(2-hydroxyphenyl) nitrone compounds of formula I are named using conventional nitrone nomenclature, i.e., the carbon atom of the carbon-nitrogen double bond (C=N) is designated the α-position and substituents on the nitrogen atom of the carbon-nitrogen double bond are given the N- prefix.

In some cases, the α-(2-hydroxyphenyl) nitrones of this invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the α-(2-hydroxyphenyl) nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Additionally, all geometric isomers of the nitrone compounds of formula I are included within the scope of this invention including, for example, all isomers (i.e. E and Z isomers) of the carbon-nitrogen double bond of the nitrone functionality.

Definitions

When describing the α-(2-hydroxyphenyl) nitrones, pharmaceutical compositions and methods of this invention, the following terms have the following meanings unless otherwise specified.

"Acyl" refers to the groups: alkyl-C(O)—, substituted alkyl-C(O)—, cycloalkyl-C(O)— and aryl-C(O)—, where alkyl, substituted alkyl, cycloalkyl, and aryl are as defined herein.

"Acylamino" refers to the group "—NRC(O)R" where each R is independently hydrogen or alkyl. Preferred acylamino groups include acetamido.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH₂), n-propenyl (—CH₂CH=CH₂), isopropenyl (—C(CH₃)=CH₂), and the like.

"Substituted alkenyl" refers to alkenyl groups preferably having from 2 to 10 carbon atoms and more preferably 2 to 6 carbon atoms and having at least 1 and preferably from 1–2 sites of alkenyl unsaturation, which are substituted with from 1 to 3 substituents selected from the group consisting of alkoxy, amino, mono- and dialkylamino, acylamino, aminocarbonyl, alkoxycarbonyl, aryloxy, carboxyl, cyano, halo, hydroxy, nitro, thioalkoxy and the like.

"Alkoxy" refers to "alkyl-O—" groups preferably having from 1 to 12 carbon atoms in the alkyl group, more preferably, 1 to 8 carbon atoms. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to alkoxy groups which are substituted with from 1 to 3 substituents selected from the group consisting of alkoxy, amino, mono- and dialkylamino, acylamino, aminocarbonyl, alkoxycarbonyl, aryloxy, carboxyl, cyano, halo, hydroxy, nitro, thioalkoxy and the like. Preferred substituted alkoxy groups include, by way of example, trifluoromethoxy and the like.

"Alkoxycarbonyl" refers to the group "—C(O)OR" where R is alkyl.

"Alkyl" refers to monovalent alkyl groups preferably having from 1 to about 12 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 6 carbon atoms.

"Substituted alkyl" refers to alkyl groups preferably having from 1 to about 12 carbon atoms, more preferably 1 to 8 carbon atoms and still more preferably 1 to 6 carbon atoms, which are substituted with from 1 to 3 substituents selected from the group consisting of alkoxy, amino, mono- and dialkylamino, acylamino, aminocarbonyl, alkoxycarbonyl, aryloxy, carboxyl, cyano, halo, hydroxy, nitro, thioalkoxy and the like. A preferred substituted alkyl group is the trifluoromethyl group.

"Alkylene" refers to divalent alkylene groups preferably having from 1 to 12 carbon atoms and more preferably 1 to 6 carbon atoms which can be straight chain or branched. This term is exemplified by groups such as methylene (—CH₂—), ethylene (—CH₂CH₂—), the propylene isomers (e.g., —CH₂CH₂CH₂— and —CH(CH₃)CH₂—) and the like.

"Alkylenedioxy" refers to "—O-alkylene-O—" groups preferably having from 1 to 10 carbon atoms and more preferably 1 to 6 carbon atoms which can be straight chain or branched. This term is exemplified by groups such as methylenedioxy (—OCH₂O—), ethylenedioxy (—OCH₂CH₂O—) and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH₂C≡CH), and the like.

"Aminocarbonyl" refers to the group "—C(O)NRR" where each R is independently hydrogen or alkyl.

"Amino" refers to the group "—NH₂".

"Substituted amino" refers to the group "—N(R)₂" where each R is independently hydrogen, alkyl, substituted alkyl or aryl, provided both R groups are not hydrogen.

"Aralkyl" refers to "aryl-alkylene-" groups preferably having from 1 to 10 carbon atoms in the alkylene moiety and from 6 to 14 carbon atoms in the aryl moiety. Such aralkyl groups are exemplified by benzyl, phenethyl, and the like.

"Aralkyloxy" refers to "aryl-alkylene-O—" groups preferably having from 1 to 10 carbon atoms in the alkylene moiety and from 6 to 14 carbon atoms in the aryl moiety. Such aralkyloxy groups are exemplified by benzyloxy, phenethyloxy, and the like.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 5 substituents, preferably 1 to 3 substituents, selected from the group consisting of alkyl, substituted alkyl, alkenyl, substituted alkenyl, alkynyl, alkylene, alkylenedioxy, cycloalkyl, aralkyl, aryl, alkoxy, substituted alkoxy, aryloxy, aralkyloxy, cycloalkoxy, acyl, acylamino, aminocarbonyl, alkoxycarbonyl, carboxyl, cyano, halo, hydroxy, nitro, sulfonate, thiol, thioalkoxy, thioalkoxycarbonyl and —NRR, where each R is independently selected from hydrogen, alkyl, substituted alkyl or aryl.

"Aryloxy" refers to "—O-aryl" groups wherein aryl is as defined herein.

"Carboxyl" refers to the group "—C(O)OH" and salts thereof.

"Cyano" refers to the group "—CN".

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Cycloalkoxy" refers to "—O-cycloalkyl" groups. Such cycloalkoxy groups include, by way of example, cyclopentoxy, cyclohexoxy and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkylalkyl" refers to "cycloalkyl-alkylene-" groups preferably having from 1 to 10 carbon atoms in the alkylene moiety and from 3 to 8 carbon atoms in the cycloalkyl moiety. Such cycloalkylalkyl groups are exemplified by —CH₂-cyclopropyl, —CH₂-cyclopentyl, —CH₂CH₂-cyclohexyl, and the like.

"Halo" or "halogen" refers to fluoro, chloro, bromo and iodo.

"Hydroxy" refers to the group "—OH".

"Nitro" refers to the group "—NO₂".

"Sulfonate" refers to the group "—SO₃H" and salts thereof.

"Thioalkoxy" or "alkylthioether" refers to "alkyl-S—" groups. Preferred thioalkoxy groups include, by way of example, thiomethoxy, thioethoxy, n-thiopropoxy, isothiopropoxy, n-thiobutoxy and the like.

"Thioalkoxycarbonyl" refers to the group "alkyl-S—C(O)—".

"Thiol" refers to the group "—SH".

"Pharmaceutically acceptable salt" refers to salts which are acceptable for administration to mammals including, by way of illustration, alkali and alkaline earth metal salts and addition salts of free acids and amines. Such pharmaceutically acceptable salts may be derived from a variety of organic and inorganic counter-ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable cation" refers to a pharmaceutically acceptable cationic counterion of an acidic functional group. Such cations are exemplified by sodium, potassium, calcium, magnesium, ammonium, tetraalkylammonium cations, and the like.

General Synthetic Procedures

The α-(2-hydroxyphenyl) nitrones of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

In a preferred method of synthesis, the α-(2-hydroxyphenyl) nitrones of this invention are prepared by coupling an aryl carbonyl compound of formula III:

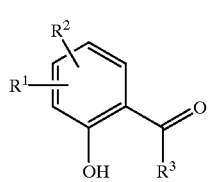

III wherein $R^1$, $R^2$ and $R^3$ are as defined above or where $R^1$ is —C(O)$R^3$, with a hydroxylamine of formula IV:

IV wherein $R^4$ is as defined above, under conventional reaction conditions.

This coupling reaction is typically conducted by contacting the aryl carbonyl compound III with at least one equivalent, preferably about 1.1 to about 2 equivalents, of hydroxylamine IV in an inert polar solvent such as methanol, ethanol, 1,4-dioxane, tetrahydrofuran, dimethyl sulfoxide, dimethylformamide and the like. This reaction is preferably conducted at a temperature of from about 0° C. to about 100° C. for about 1 to about 48 hours. Optionally, a catalytic amount of an acid, such as hydrochloric acid, acetic acid, p-toluenesulfonic acid and the like, may be employed in this reaction. When $R^1$ in formula III is —C(O)$R^3$, at least two equivalents of hydroxylamine IV are employed in this coupling reaction. Upon completion of the reaction, the α-(2-hydroxyphenyl) nitrone of formula I is recovered by conventional methods including precipitation, chromatographic separation, filtration, distillation, sublimation, and the like.

The aryl carbonyl compounds of formula III employed in the above-described coupling reaction are either known compounds or compounds that can be prepared from known compounds by conventional procedures. Representative aryl carbonyl compounds of formula III include, by way of illustration, 5-chloro-2-hydroxybenzaldehyde, 3,5-dibromo-2-hydroxybenzaldehyde, 3-fluoro-2-hydroxybenzaldehyde, 2-hydroxy-3-methylbenzaldehyde, 2-hydroxy-5-methoxybenzaldehyde, 2-hydroxy-5-nitrobenzaldehyde, 3-ethoxy-2-hydroxybenzaldehyde, 3,5-dichloro-2-hydroxybenzaldehyde, 5-bromo-2-hydroxybenzaldehyde, 4,6-dimethoxy-2-hydroxybenzaldehyde, 5-chloro-2-hydroxy-1,3-benzenedicarboxaldehyde, 2-hydroxy-5-methyl-1,3-benzenedicarboxaldehyde and the like.

The hydroxylamine compounds of formula IV above are also known compounds or compounds which can be prepared from known compounds by conventional procedures. Typically, the hydroxylamine compounds of formula IV are prepared by reducing the corresponding nitro compound (i.e., $R^4$—$NO_2$, wherein $R^4$ is as defined above) using a suitable reducing agent such as activated zinc/acetic acid, activated zinc/ammonium chloride or an aluminum/mercury amalgam. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc reagents or an ether/water mixture in the case of the aluminum amalgams. Aliphatic nitro compounds (in the form of their salts) can also be reduced to hydroxylamines using borane in tetrahydrofuran. Since some hydroxylamines have limited stability, such compounds are generally prepared immediately prior to reaction with the aryl carbonyl compound of formula III.

Preferred hydroxylamines for use in this invention include, but are not limited to, N-isopropylhydroxylamine, N-n-propylhydroxylamine, N-n-butylhydroxylamine, N-tert-butylhydroxylamine, N-cyclohexylhydroxylamine and the like.

Pharmaceutical Compositions

When employed as pharmaceuticals, the α-(2-hydroxyphenyl) nitrones of this invention are typically administered in the form of a pharmaceutical composition. Such compositions can be prepared using procedures well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by any suitable routes including, by way of illustration, oral, topical, rectal, transdermal, subcutaneous, intravenous, intramuscular, intranasal, and the like. Depending on the intended route of delivery, the compounds of this invention are preferably formulated as either oral, topical or injectable compositions.

Pharmaceutical compositions for oral administration can take the form of bulk liquid solutions or suspensions, or bulk powders. More commonly, however, such compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the nitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Topical compositions are typically formulated as a topical ointment or cream containing the active ingredient(s), generally in an amount ranging from about 0.01 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example, an oil-in-water cream base. Such topical formulations are well-known in the art and generally include additional ingredients to enhance the dermal penetration or stability of the active ingredients or the formulation. All such known topical formulations and ingredients are included within the scope of this invention.

The compounds of this invention can also be administered by a transdermal device. Accordingly, topical administration can be accomplished using a patch either of the reservoir or porous membrane type or of a solid matrix variety.

Injectable compositions are typically based upon injectable sterile saline or phosphate-buffered saline or other injectable carriers known in the art. As before, the α-(2-hydroxyphenyl) nitrone compound in such compositions is typically a minor component, often being from about 0.05 to 10% by weight with the remainder being the injectable carrier and the like.

The above-described components for orally and topically administrable or injectable compositions are merely representative. Other materials as well as processing techniques and the like are set forth in Part 8 of *Remington's Pharma-* ceutical Sciences, 18th edition, 1990, Mack Publishing Company, Easton, Pa., 18042, which is incorporated herein by reference.

The compounds of this invention can also be administered in sustained release forms or from sustained release drug delivery systems. A description of representative sustained release materials cain be found in the incorporated materials in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active nitrone compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active nitrone compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Injection

The compound of formula I is dissolved in a buffered sterile saline injectable aqueous medium to a concentration of approximately 5 mg/mL.

Formulation 5—Ointment

Stearyl alcohol (250 g) and white petrolatum (250 g) are melted at about 75° C. and then a mixture of a compound of formula I (50 g), methylparaben (0.25 g), propylparaben (0.15 g), sodium lauryl sulfate (10 g), and propylene glycol (120 g) dissolved in water (about 370 g) is added and the resulting mixture is stirred until it congeals.

Compound Utility

Among other properties, the $\alpha$-(2-hydroxyphenyl) nitrones of this invention have been discovered to inhibit the induction of inducible cylcooxygenase (COX-2) and/or to inhibit the release of physiologically active leukotrienes and/or to be effective in various in vivo arthritis models. Accordingly, the compounds and pharmaceutical compositions of this invention find use as therapeutics for treating inflammation-related conditions in mammals including humans.

In particular, the compounds of this invention have been discovered to effectively inhibit the induction of inducible cyclooxygenase (COX-2), the release of which results in prostagladin $E_2$ (PGE$_2$) synthesis. PGE$_2$ is produced by the enzyme COX as part of the arachidonic acid pathway. The enzyme COX is now known to exist in two forms, COX-1 and COX-2. COX-1 is a constitutive form of the enzyme found in most tissues and organs. COX-2, on the other hand, is an inducible form of the enzyme associated with the production of PGE$_2$ and inflammation. Without being limited to theory, it is believed that selective inhibition of COX-2 formation will provide therapeutic agents which effectively reduce inflammation with fewer or none of the side effects associated with inhibition of COX-1 and/or COX-2. Since the compounds of this invention have been discovered to inhibit the release PGE$_2$, such compounds are useful for treating diseases or conditions characterized by an overproduction or a dysregulated production of prostagladin $E_2$ including many inflammatory conditions.

Additionally, certain compounds of this invention have been discovered to inhibit the enzyme 5-lipoxygenase (5-LO). 5-LO is known to mediate the production of physiologically active leukotrienes, such as leukotriene $B_4$ (LTB$_4$), leukotriene $C_4$ (LTC$_4$) and leukotriene $D_4$ (LTD$_4$). These leukotrienes have been implicated in various inflammation-related disorders and allergic diseases. Accordingly, compounds which inhibit 5-lipoxygenase are useful for treating diseases or conditions characterized by an overproduction or a dysregulated production of leukotrienes.

Among the inflammation-related conditions which may be treated with the $\alpha$-(2-hydroxyphenyl) nitrone compounds and pharmaceutical compositions of this invention are various forms of arthritis, including be not limited to, rheumatoid arthritis, osteoarthritis, ankylosing spondylitis, systemic lupus erythematosus, psoriatic arthritis, and the like. Other inflammation-related conditions include, by way of illustration, inflammatory bowel disease (IBD), septic shock, erythema nodosum leprosy, septicemia, uveitis, adult respiratory distress syndrome (ARDS) and the like.

As discussed above, the compounds described herein are suitable for use in a variety of drug delivery systems. Injection dose levels for treating inflammation-related conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the treatment of long-term conditions, such as arthritis, the regimen for treatment may stretch over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the nitrone, with preferred doses each providing from about 0.1 to about 10 mg/kg and especially about 1 to about 5 mg/kg.

The compounds of this invention can be administered as the sole active agent or they can be administered in combination with other active agents, such as cyclooxygenase inhibitors, 5-lipoxygenase inhibitors, non-steroidal antiinflammatory drugs (NSAIDs), peripheral analgesic agents such as zomepirac, diflunisol, and the like, and other active nitrone derivatives.

The novel $\alpha$-(2-hydroxyphenyl) nitrones of this invention also find use as analytical reagents, i.e. as spin traps, for detecting unstable free radicals using electron spin resonance (ESR) spectroscopy and related techniques. When used as analytical reagents, the nitrone compounds of this invention are typically contacted with the radical to be studied in solution and an ESR spectrum generated in a conventional manner. In particular, the nitrones of this invention may be used to detect and identify free radicals in biological systems. Any ESR spectrometer, such as a JEOL JES-FE3XG spectrometer, may be employed in these experiments. Typically, the solution containing the spin-trap will be deoxygenated by, for example, bubbling argon or nitrogen through the solution before the ESR experiment is conducted. Preferably, an excess of the nitrone is used in such ESR experiments.

The actual experimental procedures employed in the spin-trapping experiment will depend on a number of factors, such as the manner of radical production, the inertness of the solvent and reagents with respect to the spin trap, the lifetime of the spin adduct and the like. Spin trapping procedures are well known in the art and the exact procedure employed can be determined by those skilled in the art. Typical procedures and apparatus for conducting spin trapping experiments are described, for example, in C. A. Evans, "Spin Trapping", *Aldrichimica Acta*, (1979), 12(2), 23–29, and references cited therein.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.

| | |
|---|---|
| bd | = broad doublet |
| bs | = broad singlet |
| d | = doublet |
| dd | = doublet of doublets |
| dec | = decomposed |
| $dH_2O$ | = distilled water |
| ELISA | = enzyme-linked immuno-sorbent assay |
| EtOAc | = ethyl acetate |
| EtOH | = ethanol |
| g | = grams |
| h | = hours |
| Hz | = hertz |
| ip | = intraperitoneal |
| L | = liter |
| m | = multiplet |
| min | = minutes |
| M | = molar |
| MeOH | = methanol |
| mg | = milligram |
| MHz | = megahertz |
| mL | = milliliter |
| mmol | = millimole |
| m.p. | = melting point |
| N | = normal |
| po | = per os, oral |
| q | = quartet |
| quint. | = quintet |
| s | = singlet |
| t | = triplet |
| THF | = tetrahydrofuran |
| tlc | = thin layer chromatography |
| $\mu g$ | = microgram |
| $\mu L$ | = microliter |
| UV | = ultraviolet |

In the examples below, all temperatures are in degrees Celsius (unless otherwise indicated). Example A–C describe the synthesis of intermediates useful for preparing nitrones of this invention; Examples 1–18 describe the synthesis of various nitrones; and Examples 19–25 describe the testing of such compounds.

Example A

Synthesis of N-tert-Butylhydroxylamine

Zinc dust (648 g) was added in portions to a cooled mixture of 2-methyl-2-nitropropane (503 g) and ammonium chloride (207 g) in deionized water (6 L) at such a rate so as to maintain the temperature below 18° C. The reaction mixture was stirred mechanically for 15 hours and then filtered. The solid was washed with hot water (1.75 L). The combined filtrate was saturated with potassium carbonate (4.6 Kg) and extracted with ethyl acetate (2×1300 mL). The organic solution was dried over anhydrous sodium sulfate, filtered and rotary evaporated to give the title compound (329 g, 75.7% yield) as white crystals. This material was used without further purification.

Spectroscopic data were as follows:

$^1$H NMR (CDCl$_3$, 270 MHz) $\delta$=1.090 (s, 3 CH$_3$).

Example B

Synthesis of N-Isopropylhydroxylamine

Using the procedure of Example A above and 2-nitropropane, the title compound was prepared. The crude hydroxylamine product was used without further purification.

Example C

Synthesis of N-Cyclohexylhydroxylamine

Using the procedure of Example A above and nitrocyclohexane, the title compound can be prepared. Alternatively, N-cyclohexylhydroxylamine hydrochloride may be purchased commercially from Aldrich Chemical Company, Inc., Milwaukee, Wis. USA and neutralized with a base, such as potassium carbonate, to provide the title compound.

Example 1

Synthesis of α-(5-Chloro-2-hydroxyphenyl)-N-tert-butylnitrone

To a solution of tert-butylhydroxylamine (14.98 g, 168.4 mmol) in MeOH (160 mL) was added 5-chloro-2-hydroxybenzaldehyde (15.8 g, 129.5 mmol) and 3 drops of 37% hydrochloric acid. The resulting solution was refluxed through a Soxhlet apparatus containing molecular sieves (40 g) until no more aldehyde was detected by TLC. The solvent was removed in vacuo and the residue was recrystallized from EtOAc. The title compound was isolated in 98.5% yield as a crystalline solid, m.p. 143.4° C. (R$_f$=0.45 on a silica gel plate using 7:10 hexanes:EtOAc as an eluant).

Spectroscopic data were as follows:

IR (KBr, cm$^{-1}$): 2976 (CH), 1571 (C=N), 1173 (N—O) and 1003 (C—O).

UV/Vis (MeOH), $\lambda_{max}$ ($\epsilon$, M$^{-1}$cm$^{-1}$): 221.5 (2.55×10$^4$), 280.5 (1.13×10$^4$), 338.5 (0.63×10$^4$).

$^1$H NMR (DMSO-d$_6$, 270 MHz) $\delta$=8.14 (1H, s, nitronyl H), 7.84 (1H, d, J=2.72 Hz, phenyl H), 7.38 (1H, dd, J=8.90, 2.72 Hz, phenyl H), 6.84 (1H, d, J=8.90 Hz, phenyl H) and 1.52 (9H, s, 3 CH$_3$).

$^{13}$C NMR (DMSO-d$_6$, 270 MHz): $\delta$=158.21, 135.55, 133.11, 131.73, 122.54, 120.81, 119.81, 70.71 and 27.81.

Example 2

Synthesis of α-(3,5-Di-tert-butyl-2-hydroxyphenyl)-N-tert-butylnitrone

The title compound was prepared according to the procedure described in Example 1 using 3,5-di-tert-butyl-2-hydroxybenzaldehyde and N-tert-butylhydroxylamine. The title compound was isolated in 82.1% yield as a crystalline solid, m.p. 234.7–235.2° C. (R$_f$=0.66 on a silica gel plate using 1:4 EtOAc/hexanes as an eluant).

Spectroscopic data were as follows:

IR (KBr, cm$^{-1}$): 2955 (CH), 1586 (C=N), 1269 (N—O) and 1023 (C—O).

$^1$H NMR (CDCl$_3$, 270 MHz) δ=11.83 (1H, s, phenolic OH), 7.80 (1H, s, nitronyl H), 7.47 (1H, d, J=2.23 Hz, phenyl H), 6.92 (1H, d, J=2.23 Hz, phenyl H), 1.64 (9H, s, 3 CH$_3$), 1.45 (9H, s, 3 CH$_3$) and 1.29 (9H, s, 3 CH$_3$).

$^{13}$C NMR (CDCl$_3$, 270 MHz): δ=156.60, 141.10, 139.97, 138.45, 128.32, 126.11, 117.53, 69.70, 35.07, 33.85, 31.14, 29.34 and 28.07.

Example 3

Synthesis of α-(3,5-Dibromo-2-hydroxyphenyl)-N-tert-butylnitrone

The title compound was prepared according to the procedure described in Example 13 using 3,5-dibromo-2-hydroxybenzaldehyde and N-tert-butylhydroxylamine. The title compound was isolated in 68.7% yield as a yellow crystalline solid, m.p. 111.3° C. ($R_f$=0.54 on a silica gel plate using 7:3 hexanes/EtOAc as an eluant).

Spectroscopic data were as follows:

IR (KBr, cm$^{-1}$): 3441 (OH), 2977 (CH), 1569 (C=N), 1247 (C—O), and 1165 (N—O).

UV/Vis (MeOH, λ$_{max}$, nm(ε, M$^{-1}$cm$^{-1}$)): 225.00 (2.75× 10$^4$), 286.00 (1.27×10$^4$), 351.00 (5.22×10$^3$).

$^1$H NMR (DMSO-d$_6$, 270 MHz): δ=8.24 (1H, s, nitronyl H), 7.99 (1H, d, J=2.1 Hz, phenyl H), 7.81 (1H, d, J=2.1 Hz, phenyl H), 1.45 (9H, s, 3 CH$_3$).

$^{13}$C NMR (DMSO-d$_6$, 270 MHz): δ=157.35, 137.43, 136.45, 134.32, 120.88, 115.09, 106.99, 70.86, 28.16.

Example 4

Synthesis of α-(3-Fluoro-2-hydroxyphenyl)-N-tert-butylnitrone

The title compound was prepared according to the procedure described in Example 1 using 3-fluoro-2-hydroxybenzaldehyde and N-tert-butylhydroxylamine. The title compound was isolated in 92.7% yield as a yellow crystalline solid, m.p. 70.3° C. ($R_f$=0.25 on a silica gel plate using 7:3 hexanes/EtOAc as an eluant).

Spectroscopic data were as follows:

IR (KBr, cm$^{-1}$): 3443 (OH), 2985 (CH), 1583 (C=N), 1239 (C—F), and 1191 (N—O).

UV/Vis (MeOH, λ$_{max}$, nm(ε, M$^{-1}$cm$^{-1}$)): 284.00 (1.05× 10$^4$).

$^1$H NMR (DMSO-d$_6$, 270 MHz): δ=8.23 (1H, s, nitronyl H), 7.33–7.30 (2H, m, 2 phenyl H), 6.83 (1H, td, J=4.78, 15.96 Hz, phenyl H), 1.55 (9H, s, 3 CH$_3$).

$^{13}$C NMR (DMSO-d$_6$, 270 MHz): δ=153.53 (d, J=242.5 Hz), 148.56 (d, J=141.51 Hz), 138.71, 129.07, 120.45 (d, J=2.07 Hz), 119.33 (d, J=18.65 Hz), 118.68 (d, J=6.22 Hz), 70.54, 27.77.

Example 5

Synthesis of α-{3-[(tert-Butyl)oxidoimino]methyl-2-hydroxy-5-methylphenyl)}-N-tert-butylnitrone The title compound was prepared according to the procedure described in Example 1 using 2-hydroxy-5-methylbenzene-1,3-dicarboxaldehyde and N-tert-butylhydroxylamine. The title compound was isolated in 93.1% yield as a yellow crystalline solid, m.p. 183.0° C. ($R_f$=0.46 on a silica gel plate using EtOAc as the eluant).

Spectroscopic data were as follows:

IR (KBr, cm$^{-1}$): 3443 (OH), 2975 (CH), 1575 (C=N), and 1126 (N—O).

UV/Vis (MeOH, λ$_{max}$, nm(ε, M$^{-1}$cm$^{-1}$)): 281.00 (8.56× 10$^3$), 376.00 (2.89×10$^3$).

$^1$H NMR (DMSO-d$_6$, 270 MHz): δ=13.45 (1H, bs, OH), 8.28 (2H, s, 2 phenyl H), 8.13 (2H, s, 2 nitronyl C), 2.24 (3H, s, CH$_3$), 1.52 (18H, s, 3 CH$_3$).

$^{13}$C NMR (DMSO-d$_6$, 270 MHz): δ=156.63, 133.60, 131.72, 126.98, 119.70, 70.49, 27.87, 20.26.

Example 6

Synthesis of α-(2-Hydroxy-3-methylphenyl)-N-tert-butylnitrone

The title compound was prepared according to the procedure described in Example 9 using 2-hydroxy-3-methylbenzaldehyde and N-tert-butylhydroxylamine. The title compound was isolated in 94% yield as a yellow crystalline solid, m.p. 59.2° C. ($R_f$=0.71 on a silica gel plate using 1:1 hexanes/EtOAc as an eluant).

Spectroscopic data were as follows:

IR (KBr, cm$^{-1}$): 3500 (OH), 2973 (CH), 1561 (C=N), and 1102 (N—O).

UV/Vis (MeOH, λ$_{max}$, nm(ε, M$^{-1}$cm$^{-1}$)): 284.00 (1.18× 10$^4$), 334.00 (4.37×10$^3$).

$^1$H NMR (CDCl$_3$, 270 MHz): δ=12.40 (1H, s, OH), 7.72 (1H, s, nitronyl H), 7.26 (1H, d, J=6.43 Hz, phenyl H), 6.93 (1H, d, J=7.92 Hz, phenyl H), 6.75 (1H, dd, J=7.63, 6.36 Hz, phenyl H), 2.27 (3H, s, CH$_3$), 1.62 (9H, s, 3 CH$_3$).

$^{13}$C NMR (CDCl$_3$, 270 MHz): δ=158.1, 137.6, 134.1, 129.9, 129.1, 118.6, 116.6, 69.9, 28.4, 16.6.

Example 7

Synthesis of α-{3-[(tert-Butyl)oxidoimino]methyl-5-chloro-2-hydroxyphenyl)}-N-tert-butylnitrone The title compound was prepared according to the procedure described in Example 9 using 5-chloro-2-hydroxybenzene-1,3-dicarboxaldehyde and N-tert-butylhydroxylamine. The title compound was isolated in 92% yield as a brown amorphous solid, m.p. 176.8 ° C. ($R_f$=0.80 on a silica gel plate using 1:1 hexanes/EtOAc).

Spectroscopic data were as follows:

IR (KBr, cm$^{-1}$): 3914 (OH), 1634 (C=N), and 1194 (N—O).

UV/Vis (MeOH, λ$_{max}$, nm(ε, M$^{-1}$cm$^{-1}$)): 279.00 (1.86× 10$^4$), 380 (7.08×10$^3$).

$^1$H NMR (CDCl$_3$, 270 MHz): δ=8.36 (2H, bs, 2 nitronyl H), 7.97 (2H, s, phenyl H), 1.62 (18H s, 6 CH$_3$).

$^{13}$C NMR (CDCl$_3$, 270 MHz): δ=157.3, 131.9, 130.7, 123.7, 120.6, 71.10, 28.31.

Example 8

Synthesis of α-(2-Hydroxy-5-methoxyphenyl)-N-tert-butylnitrone

The title compound was prepared according to the procedure described in Example 1 using 2-hydroxy-5-methoxybenzaldehyde and N-tert-butylhydroxylamine. The title compound was isolated in 68.1 % yield as a crystalline solid, m.p. 70.4–71.6° C. ($R_f$=0.23 on a silica gel plate using 3:7 EtOAc/hexanes as an eluant).

Spectroscopic data were as follows:

IR (KBr, cm$^{-1}$): 2934 (CH), 1586 (C=N), 1159 (N—O) and 1033 (C—O).

UV/Vis (MeOH), $\lambda_{max}$($\epsilon$ M$^{-1}$cm$^{-1}$): 221 (9.77×10$^3$), 282 (8.03×10$^3$), 356 (4.02×10$^3$).

$^1$H NMR (DMSO-d$_6$, 270 MHz) δ=11.68 (1H, s, phenolic OH), 8.12 (1H, s, nitronyl H), 7.20 (1H, d, J=2.97 Hz phenyl H), 6.99 (1H, dd, J=8.90, 2.97 Hz, phenyl H), 7.55 (1H, d, J=8.90 Hz, phenyl H), 3.70 (3H, s, methoxy OCH3) and 1.54 (9H, s, 3 CH3).

$^{13}$C NMR (DMSO-d$_6$, 270 MHz): δ=153.52, 152.23, 136.95, 121.22, 120.14, 118.22, 115.55, 70.25, 55.80 and 27.90.

Example 9

Synthesis of α-(2-Hydroxy-5-nitrophenyl)-N-tert-butylnitrone

A mixture of tert-butylhyroxylamine (10.5 g, 120 mmol), 2-hydroxy-5-nitrobenzaldehyde (15 g, 90 mmol) and p-toluenesulfonic acid (1.6 g, 9 mmol) in benzene (375 mL) was refluxed in a flask fitted with a Dean-Stark trap until no more aldehyde was detectable by TLC. The mixture was cooled and the resulting suspension was filtered. The title compound was isolated in 75.1% yield as a pale yellow solid, m.p. 172° C.

Example 10

Synthesis of α-(3-Ethoxy-2-hydroxyphenyl)-N-tert-butylnitrone

The title compound was prepared according to the procedure described in Example 13 using 3-ethoxy-2-hydroxybenzaldehyde and N-tert-butylhydroxylamine. The title compound was isolated in 36.4% yield as a yellow crystalline solid, m.p. 91.9° C. (R$_f$=0.25 on a silica gel plate using 1:1 EtOAc/hexanes as an eluant).

Spectroscopic data were as follows:

IR (KBr, cm$^{-1}$): 3441 (OH), 2978 (CH), 1589 (C=N), 1245 (C—O), and 1113 (N—O).

UV/Vis (MeOH, $\lambda_{max}$, nm($\epsilon$, M$^{-1}$cm$^{-1}$)): 225.00 (2.13× 10$^4$), 290.50 (1.30×10$^4$).

$^1$H NMR (CDCl$_3$, 270 MHz): δ=7.72 (1H, s, nitronyl H), 6.95 (1H, dd, J=2.1 and 7.4 Hz, phenyl H), 6.76–6.72 (2H, m, 2 phenyl H), 4.08 (2H, q, J=7.0 Hz, CH$_2$), 1.61 (9H, s, 3 CH$_3$), 1.44 (3H, t, J=7.0 Hz, CH$_3$).

$^{13}$C NMR (CDCl$_3$, 270 MHz): δ=151.01, 150.25, 137.50, 123.80, 118.74, 117.67, 116.51, 69.97, 64.65, 28.01, 15.00.

Example 11

Synthesis of α-(2-Hydroxy-4-methoxyphenyl)-N-tert-butylnitrone

The title compound was prepared according to the procedure described in Example 1 using 2-hydroxy-4-methoxybenzaldehyde and N-tert-butylhydroxylamine. The title compound was isolated in 72.9% yield as a pale yellow crystalline solid, m.p. 115.2–116.0° C. (R$_f$=0.49 on a silica gel plate using 1:1 EtOAc/hexanes as an eluant).

Spectroscopic data were as follows:

IR (KBr, cm$^{-1}$): 2982 (CH), 1591 (C=N), 1126 (N—O) and 1030 (C—O).

UV/Vis (MeOH), $\lambda_{max}$ ($\epsilon$, M$^{-1}$cm$^{-1}$): 203 (1.48×10$^4$).

$^1$H NMR (CDCl$_3$, 270 MHz) δ=13.47 (1H, s, phenolic OH), 7.53 (1H, s, nitronyl H), 6.94 (1H, d, J=8.6 Hz, phenyl H), 6.37–6.43 (2H, m, phenyl H), 3.77 (3H, s, methoxy OCH$_3$) and 1.58 (9H, s, 3 CH$_3$).

$^{13}$C NMR (CDCl$_3$, 270 MHz): δ=165.20, 162.65, 137.27, 133.99, 110.09, 107.51, 103.24, 69.07, 55.19 and 27.95.

Example 12

Synthesis of α-(4-N,N-Diethylamino-2-hydroxyphenyl)-N-tert-butylnitrone

The title compound was prepared according to the procedure described in Example 1 using 4N,N-diethylamino-2-hydroxybenzaldehyde and N-tert-butylhydroxylamine.

Example 13

Synthesis of α-(3,5-Dichloro-2-hydroxyphenyl)-N-tert-butylnitrone

To a solution of tert-butylhyroxylamine hydrochloride (1.5 eq.) and sodium methoxide (1.2 eq.) in MeOH was added 3,5-dichloro-2-hydroxybenzaldehyde (1 eq.) and 5 drops of 37% HCl. The resulting solution was refluxed over molecular sieves (40 g) until no more aldehyde was detected by TLC. The mixture was then cold filtered to remove molecular sieves and sodium chloride, and rinsed with CH$_2$Cl$_2$. The solvent was removed in vacuo and the title compound was isolated in 97.1% yield as a yellow crystalline solid, m.p. 102.9° C. (R$_f$=0.33 on a silica gel plate using 7:3 hexanes/EtOAc as an eluant).

Spectroscopic data were as follows:

IR (KBr, cm$^{-1}$): 3426 (OH), 2980 (CH), 1573 (C=N), 1247 (C—O), and 1178 (N—O).

UV/Vis (MeOH, $\lambda_{max}$, nm($\epsilon$, M$^{-1}$cm$^{-1}$)): 284.50 (1.19× 10$^4$), 346.50 (5.04×10$^3$).

$^1$H NMR (DMSO-d$_6$, 270 MHz): δ=8.24 (1H, s, nitronyl H), 7.86 (1H, s, phenyl H), 7.59 (1H, s, phenyl H), 1.52 (9H, s, 3 CH$_3$).

$^{13}$C NMR (DMSO-d$_6$, 270 MHz): δ=156.64, 136.39, 132.23, 130.76, 124.57, 70.68, 27.77.

Example 14

Synthesis of α-(5-Bromo-2-hydroxyphenyl)-N-tert-butylnitrone

The title compound was prepared according to the procedure described in Example 1 using 5-bromo-2-hydroxybenzaldehyde and N-tert-butylhydroxylamine. The title compound was isolated in 68.7% yield as a yellow crystalline solid, m.p. 118.7° C. (R$_f$=0.65 on a silica gel plate using 1:1 EtOAc/hexanes as an eluant).

Spectroscopic data were as follows:

IR (KBr, cm$^{-1}$): 3439 (OH), 2979 (CH), 1583 (C=N), 1566 (C=N), 1247 (C—O), and 1172 (N—O).

UV/Vis (MeOH, $\lambda_{max}$, nm($\epsilon$, M$^{-1}$cm$^{-1}$)): 221.50 (1.60× 10$^4$), 281.50 (7.24×10$^3$), 340.00 (3.84×10$^3$).

$^1$H NMR (DMSO-d$_6$, 270 MHz): δ=8.13 (1H, s, nitronyl H), 7.97 (1H, d, J=2.54 Hz, phenyl H), 7.48 (1H, dd, J=2.54, 8.90 Hz, phenyl H), 6.79 (1H, d, J=8.90 Hz, phenyl H), 1.54 (9H, s, 3 CH$_3$).

$^{13}$C NMR (DMSO-d$_6$, 270 MHz): δ=158.63, 135.90, 135.44, 134.66, 121.26, 120.45, 109.83, 70.69, 27.80.

Example 15

Synthesis of α-(4,6-Dimethoxy-2-hydroxyphenyl)-N-tert-butylnitrone

The title compound was prepared according to the procedure described in Example 1 using 4,6-dimethoxy-2- hydroxybenzaldehyde and N-tert-butylhydroxylamine. The title compound was isolated in 60.7% yield as a yellow crystalline solid, m.p. 97.3° C. ($R_f$=0.38 on a silica gel plate using 7:3 hexanes/EtOAc as an eluant).

Spectroscopic data were as follows:

IR (KBr, cm$^{-1}$): 3436 (OH), 2981 (CH), 1589 (C=N), and 1120 (N—O).

UV/Vis (MeOH, λmax, nm(ε, M$^{-1}$cm$^{-1}$)): 313.00 (3.45×10$^4$).

$^1$H NMR (DMSO-d$_6$, 270 MHz): δ=8.01 (1H, s, nitronyl H), 6.06 (1H, d, J=2.23 Hz, phenyl H), 5.97 (1H, d, J=2.23 Hz, phenyl H), 3.79 (3H, s, CH$_3$), 3.75 (3H, s, CH$_3$), 1.50 (9H, s, 3 CH$_3$).

$^{13}$C NMR (DMSO-d$_6$, 270 MHz): δ=166.02, 163.90, 161.11, 134.04, 100.68, 96.07, 90.40, 69.23, 56.41, 55.67, 27.77.

Example 16

Synthesis of α-(2-Hydroxy-5-trifluoromethoxyphenyl)-N-tert-butylnitrone

The title compound was prepared according to the procedure described in Example 1 using 2-hydroxy-5-trifluoromethoxybenzaldehyde and N-tert-butylhydroxylamine. The title compound was isolated in 81.8% yield as a yellow crystalline solid, m.p. 82.6° C. ($R_f$=0.40 on a silica gel plate using 7:3 hexanes/EtOAc as an eluant).

Spectroscopic data were as follows:

IR (KBr, cm$^{-1}$): 3434 (OH), 2985 (CH), 1581 (C=N), and 1171 (N—O).

UV/Vis (MeOH, $λ_{max}$, nm(ε, M$^{-1}$cm$^{-1}$)): 279.00 (1.96×10$^4$), 331.00 (1.27×10$^4$).

$^1$H NMR (DMSO-d$_6$, 270 MHz): δ=12.31 (1H, s, OH), 8.18 (1H, s, nitronyl H), 7.90 (1H, d, J=2.97 Hz, phenyl H), 7.35 (1H, dd, J=2.97, 8.25 Hz, phenyl H), 6.90 (1H, d, J=8.25 Hz, phenyl H), 1.53 (9H, s, 3 CH$_3$).

$^{13}$C NMR (DMSO-d$_6$, 270 MHz): δ=157.13, 140.50, 133.73, 126.16, 124.22, 120.75 (q, J=255.43 Hz), 119.67, 119.01, 71.11, 28.18.

Example 17

Synthesis of α-(3,5-Diiodo-2-hydroxyphenyl)-N-tert-butylnitrone

The title compound was prepared according to the procedure described in Example 1 using 3,5-diiodo-2-hydroxybenzaldehyde and N-tert-butylhydroxylamine. The title compound was isolated in 73.8% yield as a yellow crystalline solid, m.p. 164.1° C. ($R_f$=0.38 on a silica gel plate using 7:3 hexanes/EtOAc as an eluant)

Spectroscopic data were as follows:

IR (KBr, cm$^{-1}$): 3433 (OH), 2981 (CH), 1561 (C=N), and 1247 (N—O).

UV/Vis (MeOH, $λ_{max}$, nm(ε, M$^{-1}$cm$^{-1}$)): 235.00 (3.29×10$^4$), 290.50 (1.61×10$^4$), 355.00 (6.70×10$^3$).

$^1$H NMR (DMSO-d$_6$, 270 MHz): δ=8.22 (1H, s, nitronyl H), 8.14 (1H, d, J=2.23 Hz, phenyl H), 7.86 (1H, d, J=2.23 Hz, phenyl H), 1.53 (9H, s, 3 CH$_3$).

$^{13}$C NMR (DMSO-d$_6$, 270 MHz): δ=158.75, 149.25, 142.34, 138.49, 119.91, 92.26, 80.56, 70.87, 27.68.

Example 18

Synthesis of α-(3,5-Dinitro-2-hydroxyphenyl)-N-tert-butylnitrone

The title compound was prepared according to the procedure described in Example 13 using 3,5-dinitro-2-hydroxybenzaldehyde and N-tert-butylhydroxylamine. The title compound was isolated in 4.4% yield as a yellow crystalline solid, m.p. 200.3° C. ($R_f$=0.15 on a silica gel plate using 10:1 EtOAc/MeOH as an eluant).

Spectroscopic data were as follows:

IR (KBr, cm$^{-1}$): 3441 (OH), 2987 (CH), 1579 (C=N), 1350 (NO$_2$), and 1183 (N—O).

UV/Vis (MeOH, $λ_{max}$, nm(ε, M$^{-1}$cm$^{-1}$)): 264.00 (1.44×10$^4$).

$^1$H NMR (DMSO-d$_6$, 270 MHz): δ=8.94 (1H d, J=2.85 Hz, phenyl H), 8.81 (1H, d, J=2.85 Hz, phenyl H), 8.61 (1H, s, nitronyl H), 1.58 (9H, s, 3 CH$_3$).

$^{13}$C NMR (DMSO-d$_6$, 270 MHz): δ=161.77, 140.86, 136.16, 134.34, 128.62, 125.07, 121.35, 71.58, 27.42.

Example 19

Lack of Inhibition of COX-1 and COX-2

In this experiment, nitrones of formula I were tested to determine if they inhibit the enzymes cyclooxygenase 1 (COX-1) and cyclooxygenase 2 (COX-2). The inhibition of COX-1 was measured by incubating arachidonic acid with COX-1 dervied from ram seminal vesicles. The inhibition of COX-2 was measured by incubation of arachidonic acid with COX-2 derived from sheep placenta. These assays are further described in Evans et al., *Biochem. Pharmacol.*, 36:2035, 1987. In each assay, the formation of prostaglandin E$_2$ (PGE$_2$) was measured by spectrophotometric quantitation of malondialdehyde. The compounds to be tested were added to incubation solutions at a concentration of 300 μM. At this concentration, indomethacin, a known inhibitor of COX-1 and COX-2, completely inhibits both enzymes. Under the same conditions, the compounds of formula I did not significantly affected COX-1 or COX-2 at a concentration of 300 μM. These results demonstrate that the compounds of formula I are not inhibitors of the enzymes cyclooxygenase 1 (COX-1) and cyclooxygenase 2 (COX-2).

Example 20

Inhibition of 5-Lipoxygenase

In this experiment, the ability of nitrones of formula I to inhibit the enzyme 5-lipoxygenase (5-LO) is demonstrated by measuring the formation of 5-hydroxyeicosatetraenoic acid (5-HETE) by radioimmunoassay (RIA). The 5-lipoxygenase assays were run using crude enzyme preparation obtained from rat basophillic leukemia cells (RBL-1). The test compound and/or vechile was preincubated with the enzyme for 5 minutes at room temperature and the reaction was initiated by addition of arachidonic as a substrate. Following an 8 minute incubation at room temperature, the reaction was terminated by addition of citric acid and levels of 5-HETE were determined by RIA. The test compounds were screened at 30 μM and results were expressed as percent inhibition.

Example 21

Inhibition of PGE$_2$

In this experiment, the ability of nitrones of formula I to inhibit induction of prostaglandin E$_2$ (PGE$_2$) is demonstrated.

For this assay, the test compounds were solubilized in 500 μL of EtOH and then adjusted to 10 mL with complete DMEM with 1 μg/mL lipopoplysaccharide (LPS) to obtain a 10 mM solution. This solution was then diluted 1/100 to obtain a 100 µM. As a reference, indomethacin was solubilized in 500 µL DMSO and then adjusted to 50 mL with complete DMEM with 1 µg/mL LPS. This 2 mM solution was then diluted 1/200 to obtain a 10 µM solution. This solution was used as a reference. All dilutions were made with complete DMEM.

Macrophages (murine macrophages RAW 264.7) were obtained from American Type Culture Collection, Rockville, Md. They were cultured in 75 cm$^3$ flasks with DMEM (Dulbeco Modified Eagle Medium with 10% Fetal Bovine Serum, penicillin, streptomycin, and glutamine) and seeded into a 96 well plate at 20×10$^6$ cells/10 mL, 200 µL per well. At 80–100% confluence, the macrophages were washed with HBSS (with penicillin, streptomycin, and glutamine) and incubated with the test compound or a reference diluted into DMEM (with 10% FCS, penicillin, streptomycin, and glutamine) with 1 µg/mL LPS for 18 hours. The cells were then washed with HBSS and incubated with 30 µM arachidonic acid in HBSS for 15 minutes at 37° C. The supernatant was taken to determine PGE$_2$ levels using conventional procedures. Results were expressed as percent inhibition. Compounds reducing the induction of PGE$_2$ by at least about 30% compared to the control were considered effective in this assay.

Initially, test compounds were screened at 100 µM. Compounds showing activity were screened at lower concentrations to obtain an IC$_{50}$. For such screening, the stock solution was diluted in a series 1:10 dilutions to obtain 30 µM, 10 µM, 1 µM, 0.1 µM solutions. The 10 µM solution was diluted 1:3 to obtain a 3 µM solution which is then diluted in a series to produce solutions of 0.3 µM and 0.03 µM. The serial dilutions are used to determine the IC$_{50}$ of the test compound.

Example 22

Carrageenan Footpad Edema Assay

In this example, the ability of compounds of formula I to reduce carrageenan footpad edema in rats is demonstrated. This assay is commonly used to screen and evaluate anti-inflammatory drug candidates. See, for example, C. A. Winter et al., "Carrageenin-induced Edema in Hind Paw of the Rat as an Assay for Anti-inflammatory Drugs," *Proc. Sci. Exp. Biol. Med.* 111, 544–547 (1962) and references cited therein.

In this assay, a carrageenan suspension (0.5%) was prepared by mixing 50 mg of carrageenan (Type IV, λ) in 10 mL, of sterile saline solution. Male Sprague-Dawley rats (150–250 g) were then injected subcutaneously with 100 µL of the carrageenan suspension in the plantar portion of the right rear paw. The test compound (100 mg in 2 mL) or a vehicle control (2 mL) was then administered by po or ip. The initial foot paw volume was measured immediately before and 3 hours after carrageenan challenge using plethysmography (Ugo-Basile). The difference between the 3-hour and the initial paw volume was for each test group of animals was used to calculate the percent inhibition of edema achieved by the test compound at the test dose compared with vehicle control group. Compounds reducing edema by at least about 10% compared to the vehicle control group were considered to be effective in this assay.

Example 23

Mycobacterium-Induced (Adjuvant) Footpad Edema Assay

In this example, the ability of compounds of formula I to reduce adjuvant-induced footpad edema in rats is demonstrated. This assay is a model for chronic inflammation. See, for example, B. M. Weichman, "Rat Adjuvant Arthritis: A Model of Chronic Inflammation," *Pharmacological Methods in the Control of Inflammation*, 363–380 (1989) and references cited therein.

In this assay, Male Lewis rats weighing between 180–220 g were lightly anesthetized with an ip injection of 30 mg/kg of sodium pentobarbital (50 mg/mL). Desiccated *Mycobacterium butyrium* (Difco, 20 mg/mL) suspended in mineral oil was injected (50 µL) at both sides of the base of the tail under the skin. A line was tattooed on both rear paws at 5 mm above the angle of the ankle. The paw volumes, under the line, were measured by volume displacement using a plethysmometer (Ugo Basile) at the day of adjuvant injection (day 0) and on day 14. On day 14, animals with paw volumes equal to the mean of paw volumes±SD were randomized into treatment groups. Rats which fell outside±1 SD were not used in the experiment. One group received vehicle (1% methyl cellulose) by the po route and the other group received indomethacin (3 mg/kg suspended in 1% methyl cellulose). Dosing began on day 14, and continued until final assessment on day 21 post-adjuvant injection. A separate group, which did not receive adjuvant or test compound, was also monitored as a control. This group has a slightly positive volume increase when paw volumes on day 21 are subtracted from day 0 values due to growth of the rat. Indomethacin (3 mg/kg, po), a known anti-inflammation compound, significantly reduced paw volume as compared to vehicle controls. Compounds reducing paw volume by at least about 30% compared to vehicle control group were considered effective in this test.

Example 24

Collagen Arthritis Assay

In this example, the ability of compounds of formula I to reduce collagen footpad edema in rats is demonstrated. This assay is commonly used to screen and evaluate anti-inflammatory drug candidates. See, for example, Larsson et al., *Arthritis & Rheumatism*, 33:693–701, 1990 and references cited therein.

For these experiments, Female DA rats (7–8 weeks of age) were immunized with Type II collagen derived from bovine nasal septum as described in Cremer et al., *J. of Immunology*, 149:1045–1053, 1992. The collagen was dissolved and administered with incomplete Freund's adjuvant. Standard precautions were taken to avoid denaturing the collagen before its administration such as keeping the solution cold during preparation. Rats were immunized in the base of the tail on day 0. Dosing began on day 10 with rats scored on day 21 on a severity scale. Rats are scored for gait (0–3), swelling (metatarsals, ankle, carpals, metacarpals, 0–3) with the highest scores given for the most swelling or impairment. All scoring was done in a blinded manner. Compounds reducing scores by at least about 30% compared to the controls were considered effective in this assay. The arthritis was also evaluated by comparing paw weights at day 21. Compounds reducing paw weight by at least about 30% compared to the controls were also considered effective in this assay.

Assay Results

Each of the compounds of formula I tested in the above assays was found to be effective for reducing the induction of PGE$_2$ and/or effective in least one of the carrageenan, adjuvant or collagen assays.

Example 25

Electron Spin Resonance (ESR) Study

Using the following procedures, the nitrones of this invention could be shown to trap free radicals using ESR spin trapping techniques. For additional experimental details, see, for example, K. R. Maples et al., "In Vivo Detection of Free Radical Metabolites", *Free Radicals in Synthesis and Biology* (F. Minisci, ed.) pp. 423–436 (Kluwer Academic Publishers, Boston, 1989); and J. A. DeGray et al., "Biological Spin Trapping", *Electron Spin Resonance* 14:246–300 (1994). In this experiment, a t-butyl hydroperoxide/ferrous iron free radical generating system is used. This free radical generating system produces t-butyl-alkoxyl radicals, t-butyl-peroxyl radicals, and methyl radicals. If the nitrones of this invention are capable of trapping any of these radicals to form a stable radical adduct, such radical adducts should be detectable by ESR spectroscopy.

To 490 μl of a 100 mM solution of the nitrone in water is added 5 μl of 100 mM ferrous sulfate. The reaction is initiated by the addition of 5 μl of 100 mM t-butyl hydroperoxide. The final concentrations of reagents are 1 mM ferrous iron, 1 mM t-butyl hydroperoxide and 98 mM of the nitrone compound in water. Once mixed, the solution is quickly transferred into a quartz flat cell and this cell is placed in the cavity of a Bruker ESP 300 ESR spectrometer, and scanned within 5 minutes of mixing. ESR spectrometer settings are: 3480 G center field, 200 G field width, 480 seconds sweep time, 9.76 GHz frequency, 10 dB power, 1.6×10$^5$ receiver gain, 0.200 G modulation amplitude, 0.320 second time constant, and 270° phase. The resulting ESR spectrum would show that the nitrone is effective at trapping free radicals and that such compounds can be used as analytical reagents for ESR applications.

From the foregoing description, various modifications and changes in the compositions and methods of this invention will occur to those skilled in the art. All such modifications coming within the scope of the appended claims are intended to be included therein.

What is claimed is:

1. A compound of formula I:

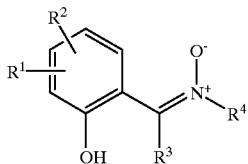

I wherein
$R^1$ is selected from the group consisting of alkyl, alkenyl, alkoxy, acylamino, amino, substituted amino, aryl, cycloalkyl, halogen, nitro and —C=N(O)—$R^5$, wherein $R^5$ is alkyl, substituted alkyl or cycloalkyl;
$R^2$ is selected from the group consisting of hydrogen, alkyl, alkenyl, alkoxy, acylamino, amino, substituted amino, aryl, cycloalkyl, halogen and nitro; or $R^1$ and $R^2$ can be joined together to form an alkylenedioxy group;
$R^3$ is selected from the group consisting of hydrogen, alkyl and aryl; and
$R^4$ is selected from the group consisting of alkyl, substituted alkyl and cycloalkyl; and pharmaceutically acceptable salts thereof.

2. The compound according to claim 1, wherein $R^1$ is selected from the group consisting of alkoxy, alkyl, halogen, nitro and —CH=N(O)—$R^5$.

3. The compound according to claim 2, wherein $R^1$ is alkyl.

4. The compound according to claim 3, wherein $R^1$ is tert-butyl.

5. The compound according to claim 2, wherein $R^2$ is selected from the group consisting of alkyl and halogen.

6. The compound according to claim 3, wherein $R^2$ is alkyl.

7. The compound according to claim 4, wherein $R^2$ is tert-butyl.

8. The compound according to claim 7, wherein $R^3$ is hydrogen.

9. The compound according to claim 8, wherein $R^4$ is selected from the group consisting of alkyl having 3 to about 8 carbon atoms and cycloalkyl having 3 to about 8 carbon atoms.

10. The compound according to claim 9, wherein $R^4$ is alkyl having 3 to 6 carbon atoms or cycloalkyl having 5 to 6 carbon atoms.

11. The compound according to claim 10, wherein $R^4$ is selected from the group consisting of n-propyl, isopropyl, n-butyl, tert-butyl and cyclohexyl.

12. A compound of formula II:

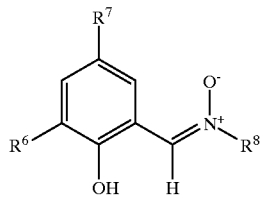

II wherein
$R^6$ is selected from the group consisting of alkyl and cycloalkyl;
$R^7$ is selected from the group consisting of alkyl and cycloalkyl; and
$R^8$ is selected from the group consisting of alkyl, substituted alkyl and cycloalkyl; and pharmaceutically acceptable salts thereof.

13. The compound according to claim 12, wherein $R^6$ and $R^7$ are the same or different and each is independently selected from an alkyl group having from 1 to about 6 carbon atoms.

14. The compound according to claim 13, wherein $R^6$ and $R^7$ are independently selected from the group consisting of methyl, ethyl, n-propyl, isopropyl, n-butyl, isobutyl, sec-butyl and tert-butyl.

15. The compound according to claim 14, wherein $R^8$ is selected from the group consisting of alkyl having 3 to about 8 carbon atoms and cycloalkyl having 3 to about 8 carbon atoms.

16. A compound selected from the group consisting of:

α-(5-chloro-2-hydroxyphenyl)-N-tert-butylnitrone
α-(3,5-di-tert-butyl-2-hydroxyphenyl)-N-tert-butylnitrone
α-(3,5-dibromo-2-hydroxyphenyl)-N-tert-butylnitrone
α-(3-fluoro-2-hydroxyphenyl)-N-tert-butylnitrone
α-{3-[(tert-butyl)oxidoimino]methyl-2-hydroxy-5-methylphenyl)}-N-tert-butylnitrone
α-(2-hydroxy-3-methylphenyl)-N-tert-butylnitrone
α-{3-[(tert-butyl)oxidoimino]methyl-5-chloro-2-hydroxyphenyl)}-N-tert-butylnitrone
α-(2-hydroxy-5-methoxyphenyl)-N-tert-butylnitrone
α-(2-hydroxy-5-nitrophenyl)-N-tert-butylnitrone
α-(3-ethoxy-2-hydroxyphenyl)-N-tert-butylnitrone
α-(2-hydroxy-4-methoxyphenyl)-N-tert-butylnitrone
α-(4-N,N-diethylamino-2-hydroxyphenyl)-N-tert-butylnitrone α-(3,5-dichloro-2-hydroxyphenyl)-N-tert-butylnitrone
α-(4,6-dimethoxy-2-hydroxyphenyl)-N-tert-butylnitrone
α-(2-hydroxy-5-trifluoromethoxyphenyl)-N-tert-butylnitrone
α-(3,5-diiodo-2-hydroxyphenyl)-N-tert-butylnitrone
α-(3,5-dinitro-2-hydroxyphenyl)-N-tert-butylnitrone and pharmaceutically acceptable salts thereof.

17. A pharmaceutical composition comprising a pharmaceutically acceptable carrier and a pharmaceutically effective amount of a compound of formula I:

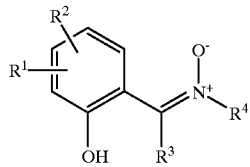

I wherein
$R^1$ is selected from the group consisting of alkyl, alkenyl, alkoxy, acylamino, amino, substituted amino, aryl, cycloalkyl, halogen, nitro and —C=N(O)—$R^5$, wherein $R^5$ is alkyl, substituted alkyl or cycloalkyl;

$R^2$ is selected from the group consisting of hydrogen, alkyl, alkenyl, alkoxy, acylamino, amino, substituted amino, aryl, cycloalkyl, halogen and nitro; or $R^1$ and $R^2$ can be joined together to form an alkylenedioxy group;

$R^3$ is selected from the group consisting of hydrogen, alkyl and aryl; and $R^4$ is selected from the group consisting of alkyl, substituted alkyl and cycloalkyl; and pharmaceutically acceptable salts thereof.

18. The pharmaceutical composition according to claim 17, wherein $R^1$ is selected from the group consisting of alkoxy, alkyl, halogen, nitro and —CH=N(O)—$R^5$.

19. The pharmaceutical composition according to claim 18, wherein $R^1$ is alkyl.

20. The pharmaceutical composition according to claim 19, wherein $R^1$ is tert-butyl.

21. The pharmaceutical composition according to claim 18, wherein $R^2$ is selected from the group consisting of alkyl and halogen.

22. The pharmaceutical composition according to claim 19, wherein $R^2$ is alkyl.

23. The pharmaceutical composition according to claim 20, wherein $R^2$ is tert-butyl.

24. The pharmaceutical composition according to claim 23, wherein $R^3$ is hydrogen.

25. The pharmaceutical composition according to claim 24, wherein $R^4$ is selected from the group consisting of alkyl having 3 to about 8 carbon atoms and cycloalkyl having 3 to about 8 carbon atoms.

26. The pharmaceutical composition according to claim 25, wherein $R^4$ is alkyl having 3 to 6 carbon atoms or cycloalkyl having 5 to 6 carbon atoms.

27. The pharmaceutical composition according to claim 26, wherein $R^4$ is selected from the group consisting of n-propyl, isopropyl, n-butyl, tert-butyl and cyclohexyl.

28. A pharmaceutical composition comprising a pharmaceutically acceptable carrier and a pharmaceutically effective amount of a compound of formula I:

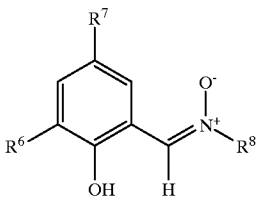

II wherein
$R^6$ is selected from the group consisting of alkyl and cycloalkyl;

$R^7$ is selected from the group consisting of alkyl and cycloalkyl; and $R^8$ is selected from the group consisting of alkyl, substituted alkyl and cycloalkyl; and pharmaceutically acceptable salts thereof.

29. The pharmaceutical composition according to claim 28, wherein $R^6$ and $R^7$ are the same or different and each is independently selected from an alkyl group having from 1 to about 6 carbon atoms.

30. The pharmaceutical composition according to claim 29, wherein $R^6$ and $R^7$ are independently selected from the group consisting of methyl, ethyl, n-propyl, isopropyl, n-butyl, isobutyl, sec-butyl and tert-butyl.

31. The pharmaceutical composition according to claim 30, wherein $R^8$ is selected from the group consisting of alkyl having 3 to about 8 carbon atoms and cycloalkyl having 3 to about 8 carbon atoms.

32. A method for treating a mammal with a condition selected from the group consisting of arthritis, rheumatoid arthritis, osteoarthritis, ankylosing spondylitis, systemic lupus erthematosus, psoriatic arthritis, inflammatory bowel disease, septic shock, erythema nodosum leprosy, septicemia, and adult respiratory distress syndrome, which method comprises administering to said mammal a pharmaceutical composition comprising a pharmaceutically acceptable carrier and an effective condition-treating amount of a compound of formula I:

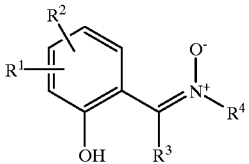

wherein
$R^1$ is selected from the group consisting of alkyl, alkenyl, alkoxy, acylamino, amino, substituted amino, aryl, cycloalkyl, halogen, nitro and —C=N(O)—$R^5$, wherein $R^5$ is alkyl, substituted alkyl or cycloalkyl;

$R^2$ is selected from the group consisting of hydrogen, alkyl, alkenyl, alkoxy, acylamino, amino, substituted amino, aryl, cycloalkyl, halogen and nitro; or $R^1$ and $R^2$ can be joined together to form an alkylenedioxy group;

$R^3$ is selected from the group consisting of hydrogen, alkyl and aryl; and $R^4$ is selected from the group consisting of alkyl, substituted alkyl and cycloalkyl; and pharmaceutically acceptable salts thereof.

33. The method according to claim 32, wherein the condition is rheumatoid arthritis.

34. The method according to claim 32, wherein the condition is osteoarthritis.

35. The method according to claim 32, wherein the condition is ankylosing spondylitis.

36. The method according to claim 32, wherein the condition is systemic lupus erythemoatosus.

37. The method according to claim 32, wherein the condition is osteoarthritis.

38. A method for inhibiting the induction of inducible cyclooxygenase (COX-2) in a mammal thereby preventing the release of prostagladin E$_2$ (PGE$_2$) synthesis, which method comprises administering to said mammal a pharmaceutical composition comprising a pharmaceutically acceptable carrier and an effective induction-inhibiting amount of a compound of formula I:

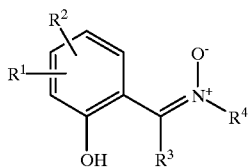

wherein

R$^1$ is selected from the group consisting of alkyl, alkenyl, alkoxy, acylamino, amino, substituted amino, aryl, cycloalkyl, halogen, nitro and —C=N(O)—R$^5$, wherein R$^5$ is alkyl, substituted alkyl or cycloalkyl;

R$^2$ is selected from the group consisting of hydrogen, alkyl, alkenyl, alkoxy, acylamino, amino, substituted amino, aryl, cycloalkyl, halogen and nitro; or R$^1$ and R$^2$ can be joined together to form an alkylenedioxy group;

R$^3$ is selected from the group consisting of hydrogen, alkyl and aryl; and

R$^4$ is selected from the group consisting of alkyl, substituted alkyl and cycloalkyl; and pharmaceutically acceptable salts thereof.

39. A pharmaceutical composition comprising a pharmaceutically acceptable carrier and a pharmaceutically effective amount of a compound of claim 16.

40. A method for treating a mammal with a condition selected from the group consisting of arthritis, rheumatoid arthritis, osteoarthritis, ankylosing spondylitis, systemic lupus erthematosus, psoriatic arthritis, inflammatory bowel disease, septic shock, erythema nodosum leprosy, septicemia, and adult respiratory distress syndrome, which method comprises administering to said mammal a pharmaceutical composition comprising a pharmaceutically acceptable carrier and an effective treating amount of a compound of claim 16.

* * * * *